United States Patent
Ogura et al.

(10) Patent No.: US 6,702,754 B2
(45) Date of Patent: Mar. 9, 2004

(54) ARTERIOSCLEROSIS INSPECTING APPARATUS

(75) Inventors: Toshihiko Ogura, Komaki (JP); Kiyoyuki Narimatsu, Komaki (JP); Akira Tampo, Komaki (JP); Takashi Honda, Komaki (JP)

(73) Assignee: Colin Corporation, Komaki (JP)

( * ) Notice: Subject to any disclaimer, the term of this patent is extended or adjusted under 35 U.S.C. 154(b) by 12 days.

(21) Appl. No.: 10/237,097

(22) Filed: Sep. 9, 2002

(65) Prior Publication Data
US 2003/0139675 A1 Jul. 24, 2003

(30) Foreign Application Priority Data
Jan. 18, 2002 (JP) ........................................ 2002-009612

(51) Int. Cl.$^7$ ................................................. A61B 5/02
(52) U.S. Cl. ........................ 600/500; 600/494; 600/483
(58) Field of Search ................................. 600/481, 483, 600/485, 486, 490, 492, 493, 494, 495, 496, 500, 501, 502, 503, 508, 509, 526

(56) References Cited
PUBLICATIONS

Yi–Xin (Jim) Wang et al.; "Reduction of Cardiac Functional Reserve and Elevation of Aortic Stiffness in Hyperlipidemic Yucatan Minipigs with Systemic and Coronary Atherosclerosis"; Vascular Pharmacology 39 (2002) pp. 69–76.

Belinda Brooks, et al. "Augmentation of Central Arterial Pressure in Type 1 Diabetes"; Diabetes Care, vol. 22, No. 10, Oct. 1999, pp. 1722–1727.

*Primary Examiner*—Max F. Hindenburg
(74) *Attorney, Agent, or Firm*—Oliff & Berridge, PLC

(57) ABSTRACT

An apparatus for inspecting arteriosclerosis of a living subject, including a pulse-wave detecting device which detects a pulse wave from a portion of the subject, an augmentation-index determining device for determining, based on the pulse wave detected by the pulse-wave detecting device, an augmentation index indicating a proportion of a reflected-wave component of the pulse wave to an incident-wave component thereof, so that the arteriosclerosis of the subject is inspected based on the augmentation index determined by the augmentation-index determining device, a waveform-related-information obtaining device which obtains waveform-related information that is related to a change of a waveform of the pulse wave detected by the pulse-wave detecting device, a display device, an augmentation-index displaying device for operating the display device to display the augmentation index determined by the augmentation-index determining device, and a waveform-related-information displaying device for operating the display device to display, in addition to the augmentation index, the waveform-related information obtained by the waveform-related-information obtaining device.

8 Claims, 12 Drawing Sheets

FIG. 3
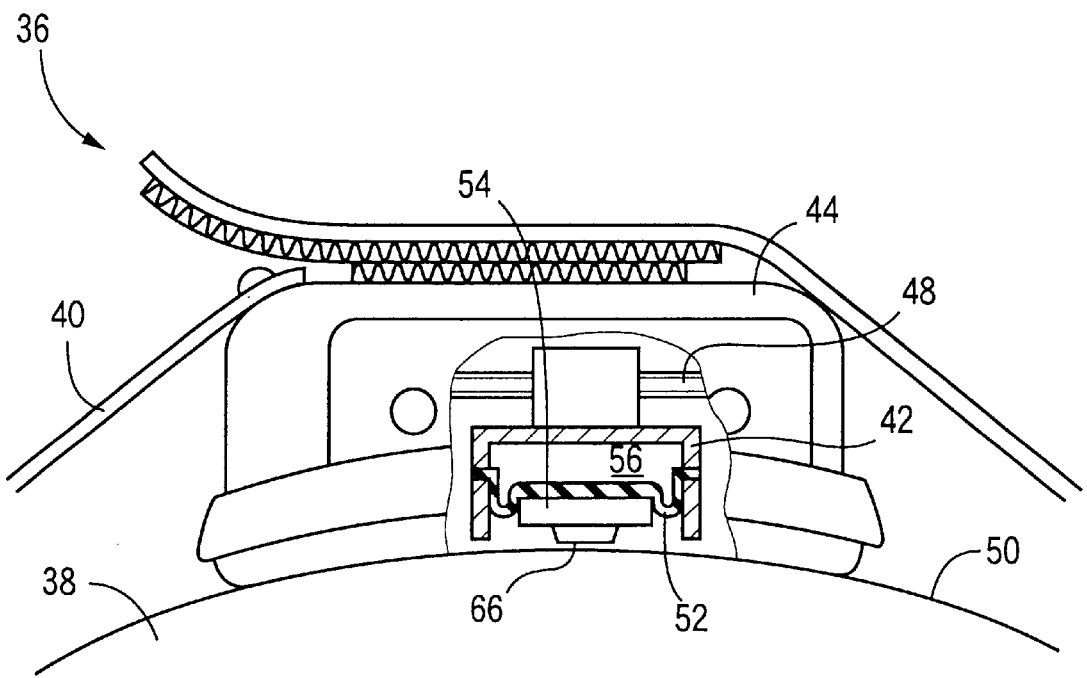

ARTERIOSCLEROSIS INSPECTING APPARATUS

BACKGROUND OF THE INVENTION

1. Field of the Invention

The present invention relates to an arteriosclerosis inspecting apparatus for inspecting arteriosclerosis of a living subject based on augmentation index.

2. Related Art Statement

Since a pulse wave that propagates in a blood vessel is reflected at a bifurcated or tapered portion of the blood vessel, a detected waveform of the pulse wave consists of an incident-wave component produced when blood is ejected from subject's heart and propagates toward subject's peripheral portion, and a reflected-wave component produced when an incident wave is reflected. Pulse-wave augmentation index, generally known as AI, indicates a proportion of a reflected-wave component of a pulse wave to an incident-wave component of the same. Usually, augmentation index AI is determined as a percentage of a value obtained by dividing, by a pulse pressure of a detected pulse wave, a difference obtained by subtracting, from a magnitude of the pulse wave at the time of occurrence of a reflected-wave component of the pulse wave, a magnitude of a peak point of an incident-wave component of the pulse wave.

As arteriosclerosis advances, the proportion of reflected-wave component of pulse wave increases and accordingly augmentation index increases. Thus, augmentation index is hopeful as an index used to evaluate arteriosclerosis.

As described above, augmentation index is determined based on the waveform of a pulse wave. However, the waveform of pulse wave is influenced by not only arteriosclerosis but also various parameters such as blood pressure. Thus, the augmentation index determined in the conventional method may largely vary or fluctuate and, at the present stage, it is difficult to evaluate arteriosclerosis based on the augmentation index only.

SUMMARY OF THE INVENTION

It is therefore an object of the present invention to provide an arteriosclerosis inspecting apparatus which assures that arteriosclerosis of a living subject can be diagnosed with high accuracy based on augmentation index.

The above object has been achieved by the present invention. According to a first aspect of the present invention, there is provided an apparatus for inspecting arteriosclerosis of a living subject, comprising a pulse-wave detecting device which detects a pulse wave from a portion of the subject; an augmentation-index determining means for determining, based on the pulse wave detected by the pulse-wave detecting device, an augmentation index indicating a proportion of a reflected-wave component of the pulse wave to an incident-wave component thereof, so that the arteriosclerosis of the subject is inspected based on the augmentation index determined by the augmentation-index determining means; at least one waveform-related-information obtaining device which obtains at least one sort of waveform-related information that is related to a change of a waveform of the pulse wave detected by the pulse-wave detecting device; a display device; an augmentation-index displaying means for operating the display device to display the augmentation index determined by the augmentation-index determining means; and a waveform-related-information displaying means for operating the display device to display, in addition to the augmentation index, the waveform-related information obtained by the waveform-related-information obtaining device.

According to this aspect of the present invention, the waveform-related-information obtaining device obtains the waveform-related information that is related to the change of the waveform of the pulse wave, and the waveform-related-information displaying means operates the display device to display, in addition to the augmentation index, the thus obtained waveform-related information. When a person inspects arteriosclerosis of the subject based on the augmentation index, the person can evaluate the augmentation index while taking into account the waveform-related information. Therefore, the person can diagnose, with improved accuracy, arteriosclerosis of the subject based on the augmentation index.

According to a preferred feature of the first aspect of the present invention, the arteriosclerosis inspecting apparatus comprises a plurality of waveform-related-information obtaining devices which obtain a plurality of sorts of waveform-related information, respectively, each of which is related to the change of the waveform of the pulse wave detected by the pulse-wave detecting device, and the waveform-related-information displaying means operates the display device to display, in addition to the augmentation index, the plurality of sorts of waveform-related information obtained by the plurality of waveform-related-information obtaining devices.

According to this feature, the display device simultaneously displays the augmentation index and the plurality of sorts of waveform-related information. Thus, the person can evaluate the augmentation index while taking into account the plurality of sorts of waveform-related information. Therefore, the person can inspect, with higher accuracy, arteriosclerosis of the subject based on the augmentation index.

According to another feature of the first aspect of the present invention, the waveform-related-information displaying means operates the display device to display, in addition to the augmentation index, a multidimensional graphical representation of the plurality of sorts of waveform-related information obtained by the plurality of waveform-related-information obtaining devices.

According to this feature, the person can easily observe, at a glance, the plurality of sorts of waveform-related information.

According to a second aspect of the present invention, there is provided an apparatus for inspecting arteriosclerosis of a living subject, comprising a pulse-wave detecting device which detects a pulse wave from a portion of the subject; an augmentation-index determining means for determining, based on the pulse wave detected by the pulse-wave detecting device, an augmentation index indicating a proportion of a reflected-wave component of the pulse wave to an incident-wave component thereof, at least one waveform-related-information obtaining device which obtains at least one sort of waveform-related information that is related to a change of a waveform of the pulse wave detected by the pulse-wave detecting device; and a corrected-augmentation-index determining means for correcting, based on the waveform-related information obtained by the waveform-related-information obtaining device, the augmentation index into a corrected augmentation index which is determined by the augmentation-index determining means when the waveform-related information obtained by the waveform-related-information obtaining device is equal to a pre-set standard value, so that the arteriosclerosis of the subject is inspected based on the corrected augmentation index determined by the corrected-augmentation-index determining means.

According to this aspect of the present invention, the waveform-related-information obtaining device obtains the waveform-related information that is related to the waveform of pulse wave that influences the augmentation index, and the corrected-augmentation-index determining means corrects the augmentation index into a corrected augmentation index which would be determined by the augmentation-index determining means if the waveform-related information would be equal to a pre-set standard value. Thus, the corrected augmentation index is freed of the influence of fluctuations of the waveform-related information, and accordingly a person can inspect, with improved accuracy, arteriosclerosis of the subject based on the corrected augmentation index.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 3 is an enlarged view of the pressure-pulse-wave detecting probe of FIG. 2, a portion of the probe being cut away;

DETAILED DESCRIPTION OF PREFERRED EMBODIMENTS

Figure 1:
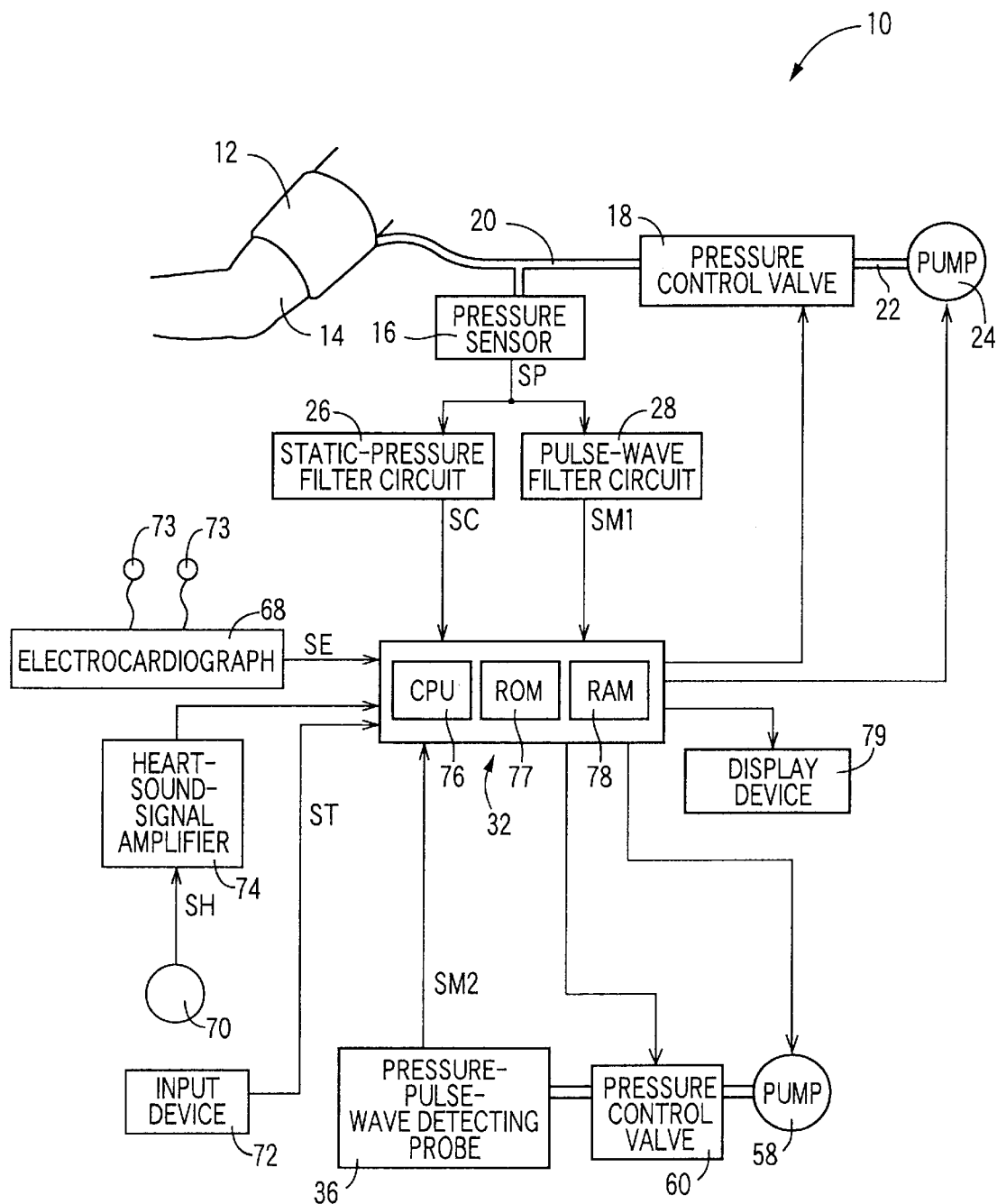
FIG. 1 is a diagrammatic view showing a circuitry of an arteriosclerosis inspecting apparatus to which the present invention is applied.

Hereinafter, there will be described an embodiment of the present invention in detail by reference to the drawings. FIG. 1 is a diagrammatic view showing a circuitry of an arteriosclerosis inspecting apparatus 10 to which the present invention is applied.

In FIG. 1, reference numeral 12 designates an inflatable cuff which includes a belt-like cloth bag and a rubber bag accommodated in the cloth bag and which is adapted to be wound around an upper portion 14 of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter that extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter, not shown. The pulse-wave filter circuit 28 includes a band-pass filter that extracts, from the pressure signal SP, a cuff-pulse-wave signal, SM1, representing an oscillatory component of the detected air pressure that has prescribed frequencies. The filter circuit 28 supplies the cuff-pulse-wave signal SM1 to the control device 32 via an A/D converter, not shown. The oscillatory component represented by the cuff-pulse-wave signal SM1 is a brachial pulse wave, wb, that is transmitted to the cuff 12 from a brachial artery, not shown, of the upper arm 14 being pressed by the cuff 12.

Figure 2:
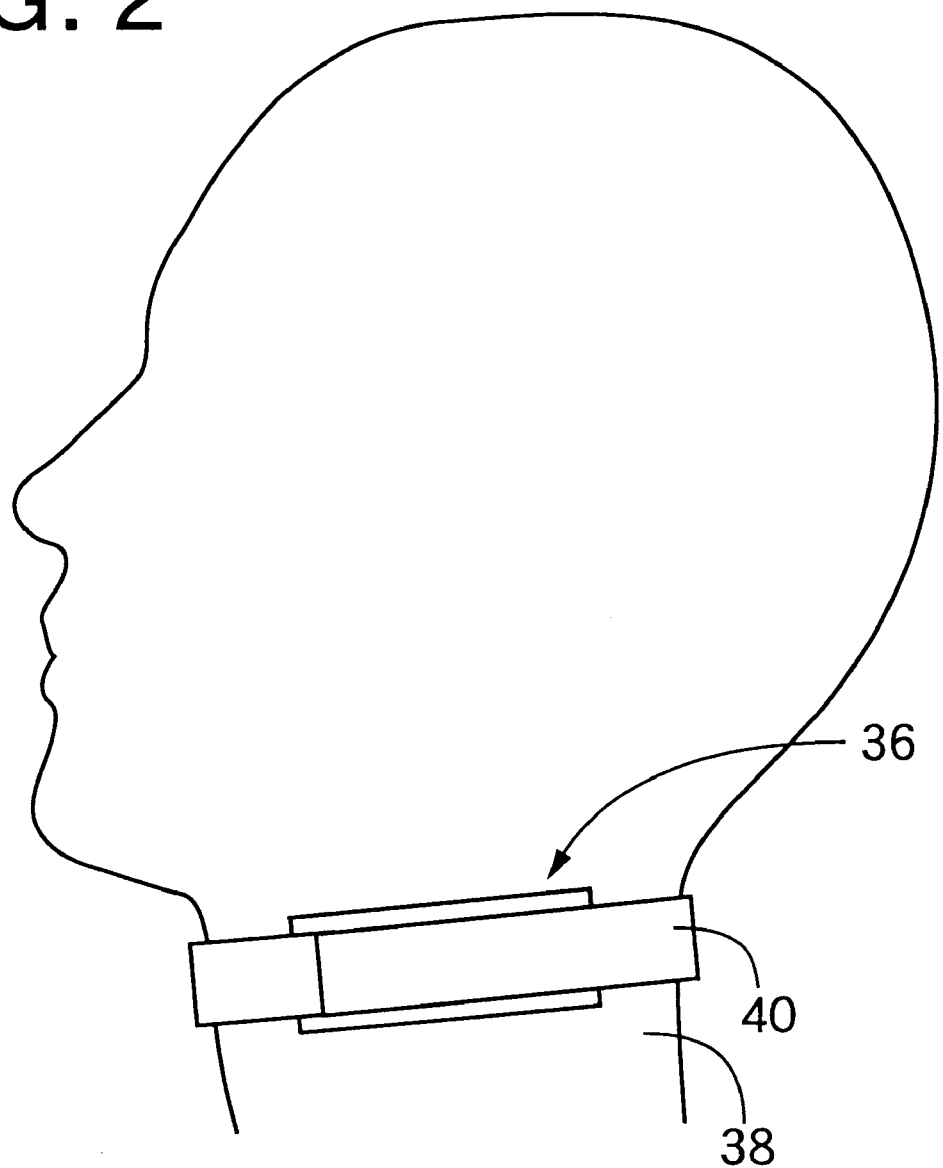
FIG. 2 is an illustrative view showing a state in which a pressure-pulse-wave detecting probe of the apparatus of FIG. 1 is worn on a neck portion of a living subject.

The present arteriosclerosis inspecting apparatus 10 includes a pressure-pulse-wave detecting probe 36, shown in FIG. 2, that functions as a carotid-pulse-wave detecting device. The pressure-pulse-wave detecting probe 36 is worn on a neck portion 38 of the subject, as illustrated in FIG. 2, with the help of a band 40. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band 40, the pressure-pulse-wave detecting probe 36 is detachably attached to the neck portion 38, such that an open end of the sensor housing 42 is opposed to a body surface 50 of the neck portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
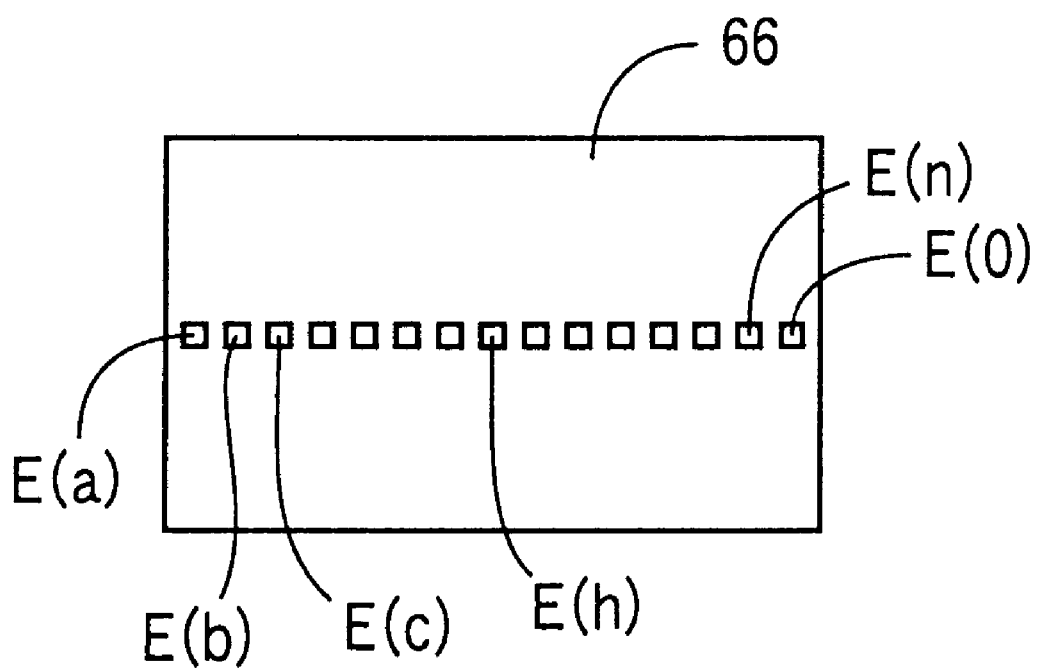
FIG. 4 is a view for explaining a state in which an array of pressure-sensing elements is provided in a press surface of a pressure-pulse-wave sensor shown in FIG. 1.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 4, fifteen pressure-sensing elements E(a), E(b), . . . , E(o) are arranged at a regular interval of, e.g., 0.6 mm.

Figure 5:
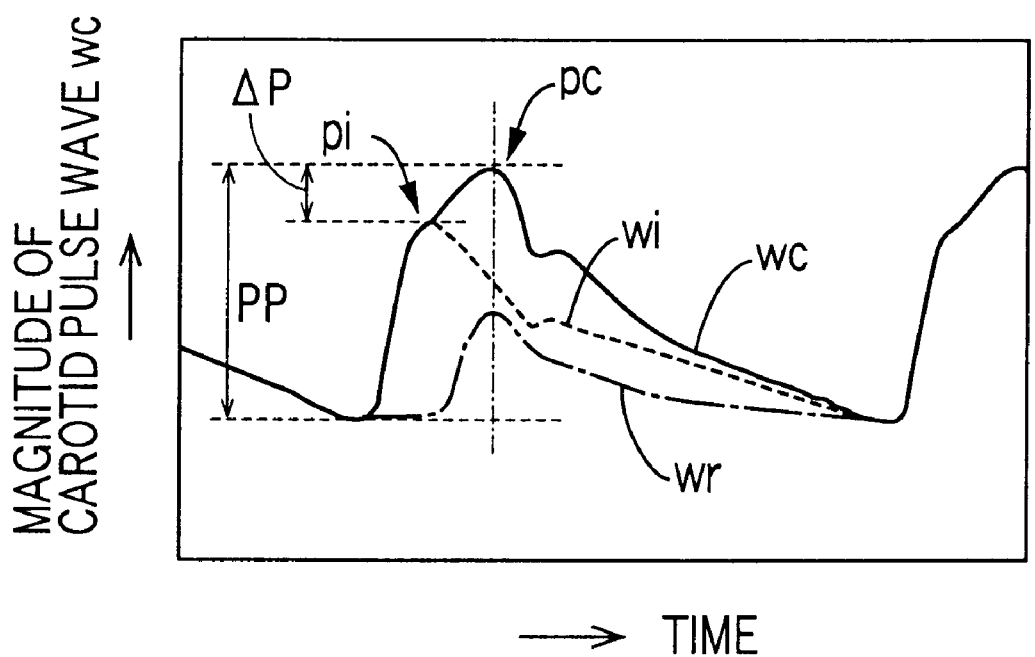
FIG. 5 is a view showing an example of a carotid pulse wave, wc, represented by a pressure-pulse-wave signal, SM2, supplied from one of the pressure-sensing elements of the pressure-pulse-wave sensor of FIG. 1.

The pressure-pulse-wave detecting probe 36, constructed as described above, is pressed against the body surface 50 of the neck portion 38 right above the carotid artery 46, so that the pressure-pulse-wave sensor 54 detects a pressure pulse wave (i.e., a carotid pulse wave, wc) which is produced from the carotid artery 46 and is propagated to the body surface 50, and supplies a pressure-pulse-wave signal SM2 representing the detected carotid pulse wave wc, to the control device 32 via an A/D converter, not shown. An example of the carotid pulse wave wc represented by the pressure-pulse-wave signal SM2 continuously supplied from the pressure-pulse-wave sensor 30 is indicated at solid line in FIG. 5.

Back to FIG. 1, the arteriosclerosis inspecting apparatus 10 further includes an electrocardiograph 68, a heart-sound microphone 70, and an input device 72. The electrocardiograph 68 includes a plurality of electrodes 73 that are attached to a body surface of the subject such that the subject's heart is positioned between the electrodes attached. The electrocardiograph 68 detects, through the electrodes 73, an action potential of the cardiac muscle, and supplies, to the control device 32 via an A/D converter, not shown, an electrocardiogram signal, SE, representing the detected action potential.

The heart-sound microphone 70 is attached, with an adhesive tape or the like, not shown, to a chest of the subject, not shown. The microphone 70 incorporates a piezoelectric element, not shown, which converts heart sounds produced from the subject's heart, into an electric signal, i.e., a heart-sound signal SH. A heart-sound-signal amplifier 74 includes four sorts of filters, not shown, which cooperate with one another to attenuate a low-pitch component having a great energy and thereby amplifies and filters a high-pitch component of the heart-sound signal SH supplied from the microphone 70. The heart-sound signal SH amplified and filtered by the amplifier 74 is supplied to the control device 32 via an A/D converter, not shown.

An input device 72 includes a plurality of keys, not shown, which are operated by an operator such as a doctor or a nurse to input a stature, T, of the subject. The input device 72 supplies a stature signal ST representing the inputted subject's stature T, to the control device 32.

The control device 32 is provided by a so-called microcomputer including a CPU (central processing unit) 76, a ROM (read only memory) 77, a RAM (random access memory) 78, and an I/O (input-and-output) port, not shown. The CPU 76 processes signals according to the control programs pre-stored in the ROM 77 by utilizing the temporary-storage function of the RAM 78, and supplies drive signals via the I/O port to the air pumps 24, 58 and the pressure control valves 18, 60 so as to control the cuff pressure PC and the pressure in the pressure chamber 56. Moreover, the CPU 76 obtains and determines, based on the cuff-pulse-wave signal SM1, the pressure-pulse-wave signal SM2, the cuff-pressure signal SC, the electrocardiogram signal SE, the heart-sound signal SH, and the stature signal ST, each supplied to the control device 32, a piece of waveform-related information, such as a blood-pressure value BP, and an augmentation index AI, and operates a display device 79 to display the thus obtained information and index.

Figure 6:
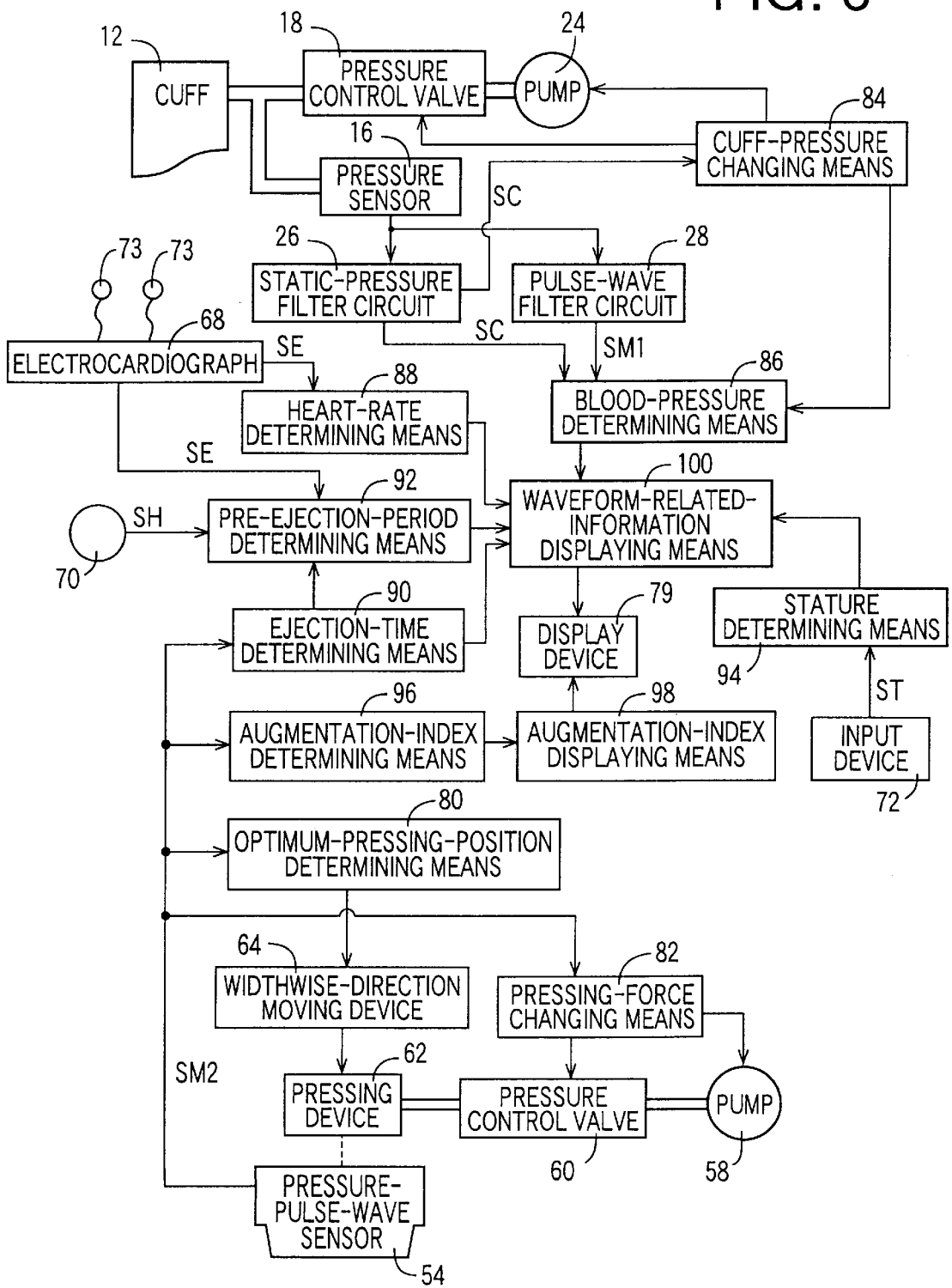
FIG. 6 is a block diagram for explaining essential control functions of an electronic control device of the apparatus of FIG. 1.

FIG. 6 is a block diagram for explaining the essential control functions of the control device 32 of the arteriosclerosis inspecting apparatus 10.

An optimum-pressing-position determining means 80 judges whether a prescribed pressing-position changing condition is satisfied, i.e., whether one (hereinafter, referred to as the "highest-pressure detecting element EM") of the pressure-sensing elements E of the pressure-pulse-wave sensor 54 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 46. When this pressing-position changing condition is satisfied, the optimum-pressing-position determining means 80 carries out the following pressing-position changing operation. After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably low first pressing force HDP1 that is smaller than an optimum pressing force HDPO, described later. In this state, the determining means 80 judges again whether the prescribed pressing-position changing condition is satisfied. The determining means 80 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing means 82 changes, after the optimum-pressing-position determining means 80 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the subject or continuously at a prescribed, considerably low rate. Based on the carotid pulse wave wc obtained during the changing of the pressing force HDP, the changing means 82 determines an optimum pressing force HDPO and maintains the pressing force applied by the pressing device 62 to the sensor 54, at the thus determined optimum pressing force HDPO. Here, the optimum pressing force HDPO is so determined that a pulse pressure PP of the carotid pulse wave wc detected by the highest-pressure detecting element EM pressed by the pressing force HDP (i.e., a difference obtained by subtracting the smallest magnitude, from the greatest magnitude, of one heartbeat-synchronous pulse of the carotid pulse wave wc) may not be smaller than a predetermined lower-limit pulse pressure $PP_L$. The lower-limit pulse pressure $PP_L$ is experimentally pre-determined as a value which assures that a clear carotid pulse wave wc can be detected. If the pulse pressure PP is too small, a clear carotid pulse wave wc cannot be obtained.

A cuff-pressure changing means 84 operates, based on the cuff-pressure signal SC supplied from the static-pressure filter circuit 26, the pressure control valve 18 and the air pump 24 so as to quickly increase the cuff pressure PC to a prescribed increase-target pressure (e.g., 180 mmHg) that would be higher than a systolic blood pressure $BP_{SYS}$ of the patient and, subsequently, slowly decrease the cuff pressure at a rate of, e.g., 2 or 3 mmHg/sec. After a blood-pressure determining means 86, described below, determines blood-pressure values BP of the patient, the changing means 84 releases the cuff pressure to an atmospheric pressure.

The blood-pressure determining means 86 determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 84, a systolic blood pressure $BP_{SYS}$, a mean blood pressure $BP_{MEAN}$, and a diastolic blood pressure $BP_{DIA}$ of the patient, according to well-known oscillometric method. The thus determined systolic blood pressure $BP_{SYS}$ corresponds to a peak point of each of successive heartbeat-synchronous pulses of the brachial pulse wave wb. Therefore, as systolic blood pressure $BP_{SYS}$ increases, magnitude of peak point of each heartbeat-synchronous pulse of brachial pulse wave wb also increases. In addition, as magnitude of peak point of each heartbeat-synchronous pulse of brachial pulse wave wb changes, magnitude of peak point pc of each heartbeat-synchronous pulse of carotid pulse wave wc also changes. Thus, as systolic blood pressure $BP_{SYS}$ changes, magnitude of peak point pc of each heartbeat-synchronous pulse of carotid pulse wave wc also changes, and accordingly waveform of each heartbeat-synchronous pulse of carotid pulse wave wc also changes. Therefore, systolic blood pressure $BP_{SYS}$ c is a sort of waveform-related information that is related to waveform of a pulse wave, and the blood-pressure determining means 86 functions as a sort of waveform-related-information obtaining means.

A heart-rate determining means 88 determines, as a pulse period, RR (sec), a time interval between respective prescribed periodic portions (e.g., respective R-waves) of two successive heartbeat-synchronous pulses of the electrocardiographic pulse wave (i.e., electrocardiogram) represented by the electrocardiogram signal SE continuously supplied from the electrocardiograph 68, and determines a heart rate, HR, (/minute) by multiplying the inverse of the pulse period RR (i.e., 1/RR) by 60. Change of heart rate HR indicates change of time interval between respective rising points of two successive heartbeat-synchronous pulses of pulse wave. Therefore, as heart rate HR change, waveform of pulse wave also changes. Thus, heart rate HR is a sort of waveform-related information, and the heart-rate determining means 88 functions as a sort of waveform-related-information obtaining means.

Figure 7:
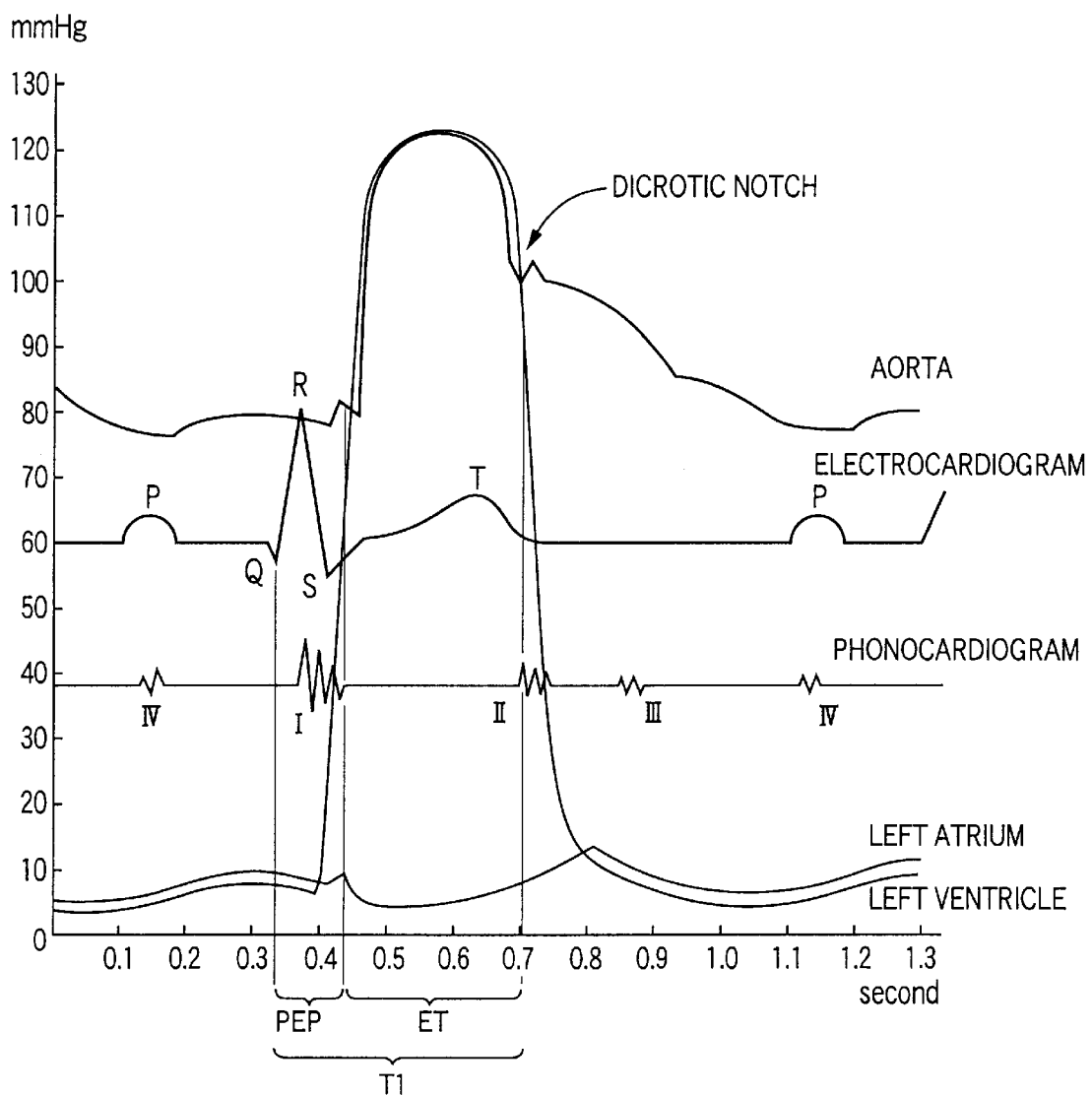
FIG. 7 is a schematic view showing pressure in aorta, pressure in left atrium, pressure in left ventricle, electrocardiogram, and electrophonogram along a common time axis.

An ejection-time determining means 90 iteratively and non-invasively determines an ejection time, ET, in which aortic valve is opened and blood is ejected from left ventricle of the subject. FIG. 7 schematically shows pressure in aorta, pressure in left atrium, pressure in left ventricle, electrocardiogram, and electrophonogram along a common time axis. As shown in FIG. 7, a time difference between rising point, and dicrotic notch, of aortic pulse wave can be determined as ejection time ET. Meanwhile, since waveform of carotid pulse wave wc is similar to waveform of aortic pulse wave, carotid pulse wave wc can be used in place of aortic pulse wave. Thus, a time difference between rising point, and dicrotic notch, of carotid pulse wave wc continuously detected by the pressure-pulse-wave sensor 54 is determined as ejection time ET. Ejection time ET is a magnitude of an incident-wave component of a pulse wave as seen in a direction parallel to the time axis. Therefore, as ejection time ET changes, waveform of the pulse wave also changes. Thus, ejection time ET is a sort of waveform-related information, and the ejection-time determining means 90 functions as a sort of waveform-related-information obtaining means.

A pre-ejection-period determining means 92 non-invasively determines a pre-ejection period, PEP, i.e., a time period between start point of systolic time of the heart and opening of aorta, i.e., starting of ejection of blood. For example, first, the pre-ejection-period determining means 92 determines a time, T1, between a time when the electrocardiograph 68 detects a wave (Q-wave, R-wave, or S-wave) indicative of excitation of ventricular muscle, and a time when the heart-sound microphone 70 detects a start point of a second heart sound II. As shown in FIG. 7, the thus determined time T1 is equal to a sum of pre-ejection period PEP and ejection time ET. Therefore, the pre-ejection-period determining means 92 determines the pre-ejection period PEP by subtracting, from the time T1, the ejection time ET determined by the ejection-time determining means 90. Since pre-ejection period PEP is a time period from starting of contraction of cardiac muscle of left ventricle to starting of ejection of blood, it is also called isovolumetric contraction time. As pre-ejection period PEP increases, pressure at the time of starting of ejection of blood also increases, and accordingly the ejection time decreases. Thus, as pre-ejection period PEP changes, waveform of pulse wave also changes. Therefore, pre-ejection period PEP is a sort of waveform-related information, and the pre-ejection-period determining means 92 functions as a sort of waveform-related-information obtaining means.

A stature determining means 94 determines, based on the stature signal ST supplied from the input device 72, a stature T of the subject. A pulse wave is composed of an incident-wave component and a reflected-wave component, as described previously, and it is speculated that the reflected wave is mainly produced at a bifurcated portion of a common iliac artery. As stature T varies, distance between the position where the pulse wave is detected and the bifurcated portion of common iliac artery also varies and accordingly time needed for the reflected wave to reach the position where the pulse wave is detected also varies. Therefore, as stature T varies, amount of overlapping of the incident-wave and reflected-wave components also varies. Thus, stature T is a sort of waveform-related information, and the stature determining means 94 functions as a sort of waveform-related-information obtaining means.

An augmentation-index determining means 96 determines, first, respective times of occurrence of respective peak points, pi and pr, of incident-wave and reflected-wave components, wi and wr, which are contained in a heartbeat-synchronous pulse of the carotid pulse wave wc continuously detected by the highest-pressure detecting element EM of the pressure-pulse-wave sensor 54 in the state in which the pressing force HDP applied to the sensor 54 is maintained at the optimum pressing force HDPO. Then, the augmentation-index determining means 96 determines a pressure difference ΔP by subtracting a magnitude of the carotid pulse wave wc at the time of occurrence of peak point pi of incident-wave component wi from a magnitude of the carotid pulse wave wc at the time of occurrence of peak point pr of reflected-wave component wr, and additionally determines a pulse pressure PP by subtracting the smallest magnitude of the heartbeat-synchronous pulse of the carotid pulse wave wc from the greatest magnitude of the same. Moreover, the determining means 96 substitutes, for the following Expression 1, the pressure difference ΔP and the pulse pressure PP, so as to determine an augmentation index AI:

$$AI=(\Delta P/PP) \times 100(\%) \qquad \text{(Expression 1)}$$

Here, the manner in which the time of occurrence of peak point pi of incident-wave component wi of the carotid pulse wave wc is determined is described. The carotid pulse wave wc contains the incident-wave component wi, indicated at broken line in FIG. 5, and the peak point pi of the incident-wave component wi corresponds to an inflection point or a maximal point of the composite carotid pulse wave (i.e., observed pulse wave) wc that occurs between a rising point and a peak point pc of the composite pulse wave wc. In the example shown in FIG. 5, the peak point pi of the incident wave wi corresponds to an inflection point of the observed pulse wave wc. To this end, the continuously obtained pressure-pulse-wave signal SM2 is subjected to a common treatment to detect an inflection point or a maximal point. Here, the common treatment may be a differentiation treatment or a filter treatment.

Generally, the time of occurrence of the peak point of the reflected wave wr is a time of occurrence of the first maximal point following the peak point pi of the incident wave wi. Therefore, in the case, shown in FIG. 5, where a peak point pi of an incident wave wi does not coincide with a peak point pc of a carotid pulse wave wc, a time of occurrence of peak point pc of the carotid pulse wave wc is determined as a time of occurrence of a peak point of a reflected wave wr. On the other hand, in the case where a peak point pi of an incident wave wi is so large that the peak point pi of the incident wave wi also defines a peak point of a carotid pulse wave wc, a time of occurrence of the first maximal point following the peak point pi of the incident wave wi is determined as a time of occurrence of a peak point of a reflected wave wr.

An augmentation-index displaying means 98 operates the display device 79 to display the augmentation index AI determined by the augmentation-index determining means 96.

A waveform-related-information displaying means 100 operates the display device 79 to display, together with the augmentation index AI, the respective sorts of waveform-related information obtained by the above-described plural sorts of waveform-related-information obtaining means. More specifically described, the waveform-related-information displaying means 100 operates the display device 79 to display, together with the augmentation index AI, the systolic blood pressure $BP_{SYS}$ determined by the blood-pressure determining means 86, the heart rate HR determined by the heart-rate determining means 88, the ejection time ET determined by the ejection-time determining means 90, the pre-ejection period PEP determined by the pre-ejection-period determining means 92, and the stature T determined by the stature determining means 94. The displaying mans 100 may operate the display device 79 to display each sort of waveform-related information, either in digits or in graphics.

Since the display device 79 simultaneously displays the augmentation index AI and the various sorts of waveform-related information, a medical person such as a doctor or a nurse can simultaneously observe the augmentation index AI and the sorts of waveform-related information. In addition, since the augmentation index AI is determined based on the waveform, the medical person can accurately evaluate arteriosclerosis of the subject based on the augmentation index AI, if the person simultaneously observe the sorts of waveform-related information. According to the experiments performed by the Inventors, there are the following relationships between the augmentation index AI and each of the sorts of waveform-related information: There is a positive correlation between the augmentation index AI and the systolic blood pressure $BP_{SYS}$ or the ejection time ET; and there is a negative correlation between the augmentation index AI and the heart rate HR, the pre-ejection period PEP, or the stature T. Therefore, if a measured systolic blood pressure $BP_{SYS}$ or a measured ejection time ET is higher or longer than an average value, or if a measured heart rate HR, a measured pre-ejection period PEP, or an inputted or measured stature T is smaller or shorter than an average value, an augmentation-index value AI displayed on the display device 79 should be evaluated as a somewhat smaller value in making a more accurate diagnosis on arteriosclerosis. Conversely, if a measured systolic blood pressure $BP_{SYS}$ or a measured ejection time ET is lower or shorter than an average value, or if a measured heart rate HR, a measured pre-ejection period PEP, or an inputted or measured stature T is greater or longer than an average value, an augmentation-index value AI displayed on the display device 79 should be evaluated as a somewhat greater value in making a more accurate diagnosis on arteriosclerosis.

Figure 8:
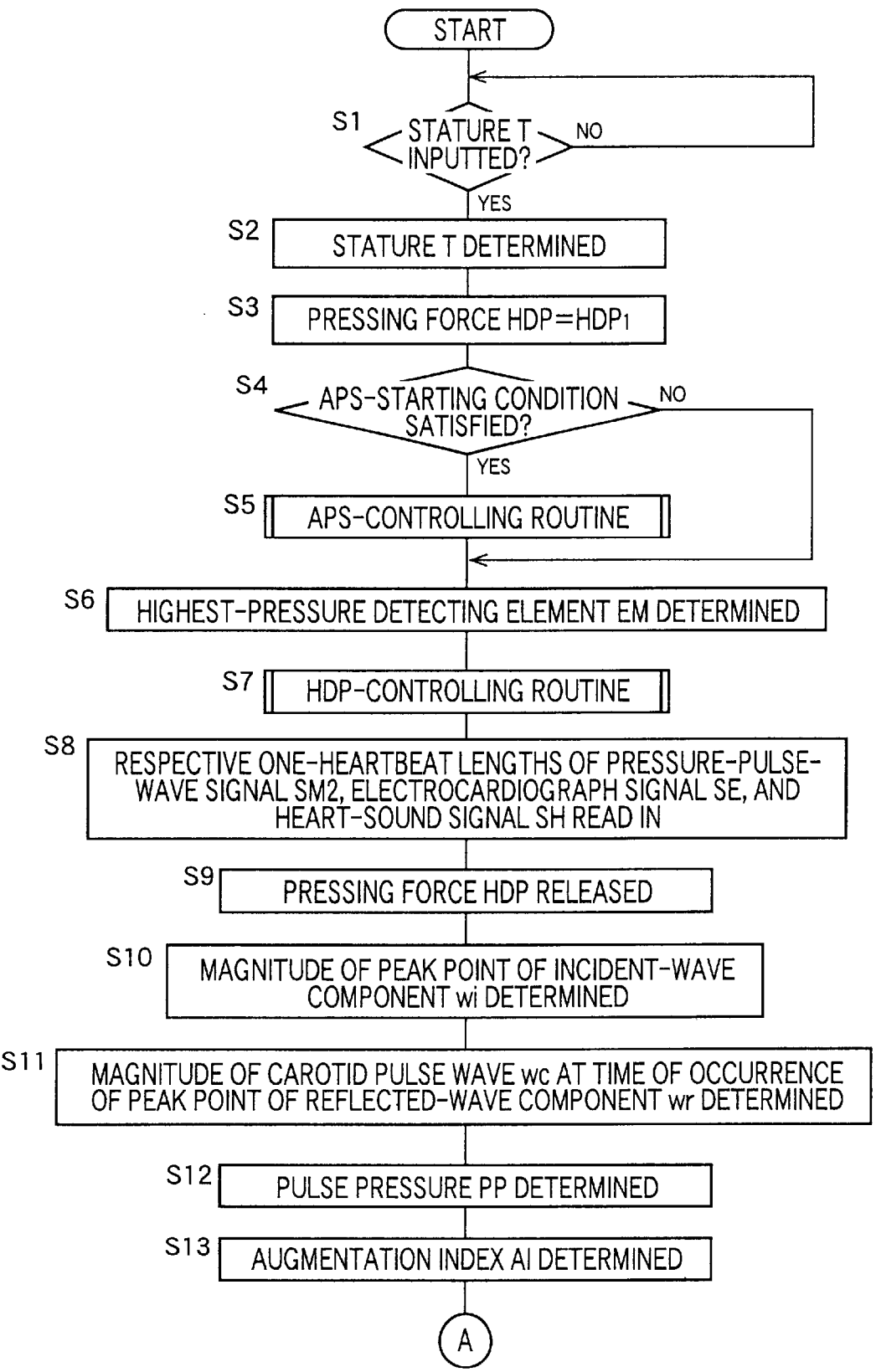
FIG. 8 is a flow chart for explaining more concretely a portion of the control functions of a CPU (central processing unit) of the control device, shown in FIG. 6.
Figure 9:
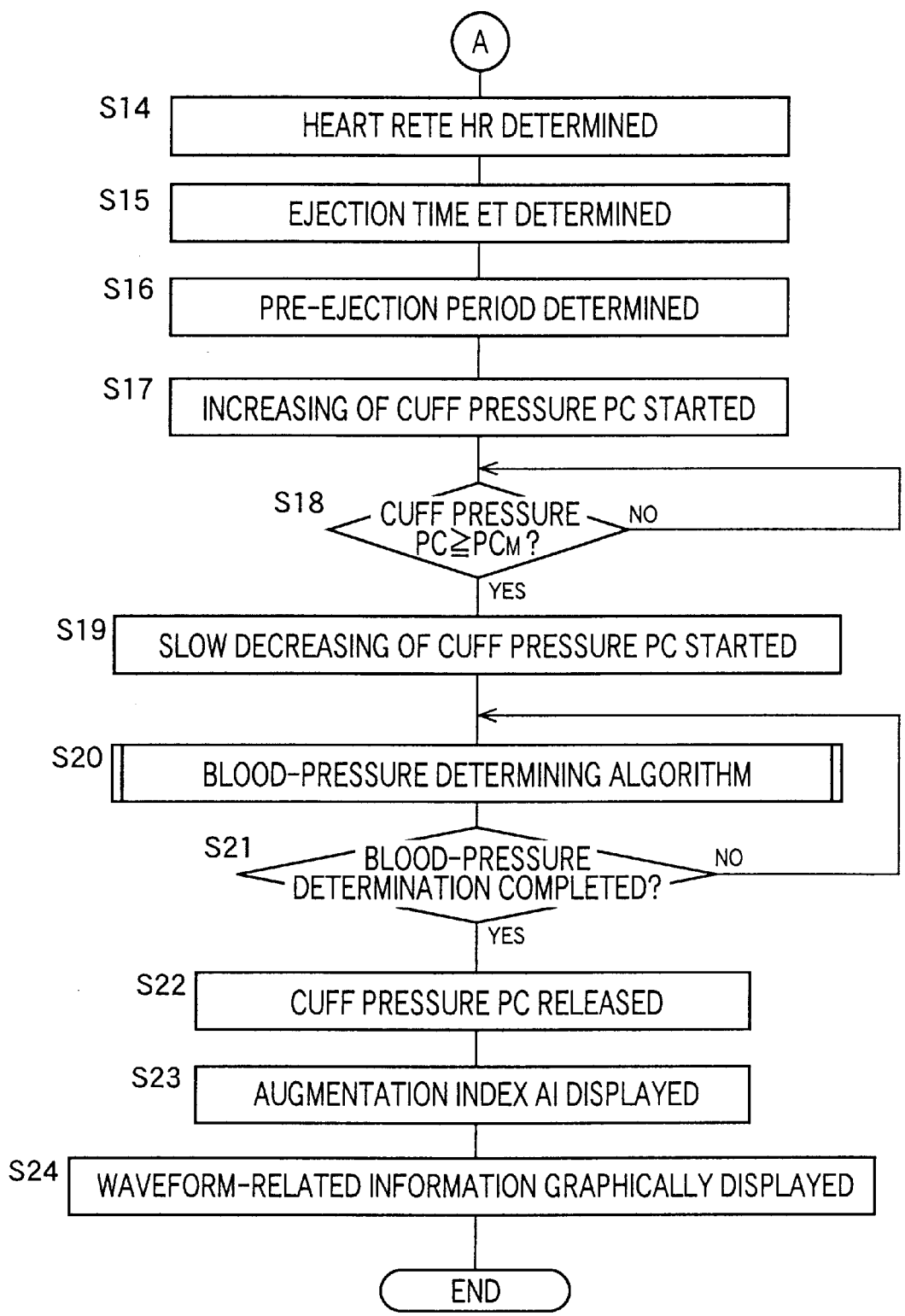
FIG. 9 is a flow chart for explaining more concretely another portion of the control functions of the CPU, shown in FIG. 6.

FIGS. 8 and 9 are flow charts representing the control functions of the CPU 76, shown in the diagrammatic view of FIG. 6.

In FIG. 8, first, the CPU carries out Step S1 (hereinafter, each term "Step(s)" is omitted). At S1, the CPU judges whether the input device 72 has been operated to input a stature T of a living subject, i.e., whether the CPU has received a stature signal ST from the input device 72. S1 is repeated until a positive judgment is made. Meanwhile, if a positive judgment is made at S1, the control goes to S2 corresponding to the stature determining means 94. At S2, the CPU determines or identifies a stature T of the subject based on the stature signal ST supplied from the input device 72.

Then, the control goes to S3 to S5 corresponding to the optimum-pressing-position determining means 80. First, at S3, the CPU operates the pressing device 62 to change the pressure in the pressure chamber 56 and thereby change the pressing force HDP applied to the pressure-pulse-wave sensor 54, to a pre-set first pressing force HDP1. This first pressing force HDP1 is experimentally determined, in advance, as a pressing force HDP that assures that respective S/N ratios of respective carotid pulse waves wc detected by the respective pressure-sensing elements E are so great as to be able to determine respective magnitudes of respective peak points pc of those carotid pulse waves wc.

Then, at S4, the CPU judges whether a pressing-position updating condition (i.e., an APS starting condition) has been satisfied, e.g., whether one EM of the pressure-sensing elements E provided in the press surface 66 of the sensor 54 that detects the highest one of the respective pressures detected by all the elements E is located in one of prescribed opposite end portions of the array of elements E. If a negative judgment is made at S3, the control goes to S6, described later.

On the other hand, if a positive judgment is made at S4, i.e., if a current position of the pressure-pulse-wave sensor 54 relative to the carotid artery 46 is not appropriate, the control goes to S5 to perform an APS-controlling routine. In this routine, the CPU operates for moving the sensor 54 to an optimum pressing position where the highest-pressure detecting element EM is located at substantially the middle of the array of elements E. More specifically, first, the CPU operates the pressing device 62 to once move the sensor 54 off the body surface 50, subsequently operates the widthwise-direction moving device 64 to move the pressing device 62 and the sensor 54 over a predetermined distance, and then operates the pressing device 62 to press again the sensor 54 at the first pressing force HDP1. In this state, the CPU judges whether the highest-pressure detecting element EM is located in a prescribed middle range of the array of pressure-sensing elements E. The above-described pressing and judging operations are repeated until a positive judgment is made.

If at S5 the pressure-pulse-wave sensor 54 is positioned at the optimum pressing position, or if a positive judgment is made at S4, the control goes to S6 to identify the highest-pressure detecting element EM in the current condition, and then to S7 corresponding to the pressing-force determining means 82, i.e., an HDP-controlling routine. More specifically described, the CPU operates the pressing device 62 so that the pressing force HDP applied to the sensor 54 is continuously increased from the first pressing force HDP1. During this increasing of the pressing force HDP, the CPU determines an optimum pressing force HDPO at which a pulse pressure PP of the carotid pulse wave wc detected by the highest-pressure detecting element EM, determined at S6, is greater than a pre-set lower-limit pulse pressure $PP_L$, and maintains the pressing force HDP applied to the sensor 54, at the thus determined optimum pressing force HDPO.

Then, the control goes to S8 where the CPU reads in the pressure-pulse-wave signal SM2 supplied from the highest-pressure detecting element EM of the pressure-pulse-wave sensor 54, the electrocardiogram signal SE supplied from the electrocardiograph 68, and the heart-sound signal SH supplied from the heart-sound microphone 70, during a time period between a time of detection of one R-wave represented by the signal SE and a time of detection of the next R-wave. Thus, the CPU reads in one heartbeat-synchronous pulse of each of the signal SM2, the signal SE, and the signal SH. Then, the control goes to S9 to stop the air pump 58 and operate the pressure control valve 60 so that the pressing force HDP applied to the sensor 54 is decreased to an atmospheric pressure.

Next, the control goes to S10 to S13 corresponding to the augmentation-index determining means 96. At S10, the CPU subjects, to a fourth-order differentiation treatment or analysis, a portion of the one heartbeat-synchronous pulse of the carotid pulse wave wc, read in at S8, that continues from a time corresponding to a rising point of the one pulse and to a time corresponding to a peak point pc of the same pulse, and thereby determines an inflection point or a maximal point occurring to the portion between the rising point and the peak point pc, and then determines a magnitude of the thus determined inflection or maximal point as a magnitude of a peak point pi of an incident wave wi.

Then, the control goes to S11 where the CPU determines a time of occurrence of a peak point of a reflected wave wr of the one pulse of the carotid pulse wave wc read in at S8, and determines a magnitude of the carotid pulse wave wc at the thus determined time of occurrence of the peak point of the reflected wave wr. More specifically described, if the magnitude of the peak point pi of the incident wave wi determined at S10 does not coincide with the greatest magnitude of the observed carotid pulse wave wc, a magnitude of the carotid pulse wave wc at a time of occurrence of the greatest magnitude of the carotid pulse wave wc is determined as a magnitude of the carotid pulse wave wc at the time of occurrence of the peak point of the reflected wave wr; and if the magnitude of the peak point pi of the incident wave wi coincides with the greatest magnitude of the observed carotid pulse wave wc, a magnitude of the carotid pulse wave wc at a time of occurrence of the first maximal magnitude following the peak point pi of the incident wave wi is determined as a magnitude of the carotid pulse wave wc at the time of occurrence of the peak point of the reflected wave wr.

Then, at S12, the CPU determines a pulse pressure PP of the one pulse of the carotid pulse wave wc read at S8. Subsequently, at S13, the CPU determines a pressure difference ΔP by subtracting the magnitude of the peak point pi of the incident wave wi, determined at S10, from the magnitude of the carotid pulse wave wc at the time of occurrence of the peak point of the reflected wave wr, determined at S11. The CPU substitutes, for the augmentation-index calculating formula represented by Expression 1, the thus determined pressure difference ΔP, and the pulse pressure PP determined at S12, so as to determine an augmentation index AI (%).

Next, there will be described S14 and the following steps shown in FIG. 9. First, at S14 corresponding to the heart-rate determining means 88, the CPU determines a pulse period RR equal to a time interval between respective R-waves of two successive heartbeat-synchronous pulses of the electrocardiogram signal SE read in at S8, and calculates a heart rate HR (/minute) by multiplying the inverse (1/RR) of the pulse period RR by 60.

Then, the control goes to S15 corresponding to the ejection-time determining means 90. At S15, the CPU determines a rising point and a dicrotic notch of the one heartbeat-synchronous pulse of the carotid pulse wave wc read in at S8, and determines, as an ejection time ET, a time difference between respective times of occurrence of the rising point and the dicrotic notch.

Subsequently, the control goes to S16 corresponding to the pre-ejection-period determining means 92. At S16, the CPU determines a start point of a second heart sound II of the heart-sound waveform (i.e., phonocardiogram) read in at S8, determines a time period T1 from a time of occurrence of an R-wave of the electrocardiogram to a time of occurrence of the start point of the second heart sound II, and finally determines a pre-ejection period PEP by subtracting, from the time period T1, the ejection time ET determined at S15.

Then, the control goes to S17 to S22 to measure blood-pressure values BP of the subject. First, at S17, the CPU starts the air pump 24 and operate the pressure control valve 18 so as to start quickly increasing the cuff pressure PC. Subsequently, at S18, the CPU judges whether the cuff pressure PC has exceeded an increase-target pressure $PC_M$ pre-set at 180 mmHg. S18 is repeated until a positive judgment is made, while the cuff pressure PC is quickly increased. Meanwhile, if a positive judgment is made at S18, the control goes to S19 to stop the air pump 24 and operate the pressure control valve 18 so as to start slowly decreasing the cuff pressure PC at a rate of about 3 mmHg/sec.

Next, the control goes to S20 and S21 corresponding to the blood-pressure determining means 86. At S20, the CPU determines, based on change of respective amplitudes of successive heartbeat-synchronous pulses of the upper-arm pulse wave represented by the cuff-pulse-wave signal SM1 continuously obtained during the slow decreasing of the cuff pressure PC, a systolic blood pressure $BP_{SYS}$, a mean blood pressure $BP_{MEAN}$, and a diastolic blood pressure $BP_{DIA}$ of the subject, according to well-known oscillometric blood-pressure determining algorithm. Then, at S21, the CPU judges whether the determination of the blood-pressure values BP has completed at S20. Since the diastolic blood pressure $BP_{DIA}$ is last determined at S20, the CPU judges, at S21, whether the diastolic blood pressure $BP_{DIA}$ has been determined. S20 is repeated until a positive judgment is made at S21, while the blood-pressure determining algorithm is continued.

Meanwhile, if a positive judgment is made at S21, the control goes to S22 to operate the pressure control valve 18 to decrease the cuff pressure PC to an atmospheric pressure. In the present flow charts, S17 to S19 and S22 correspond to the cuff-pressure changing means 84.

Figure 10:
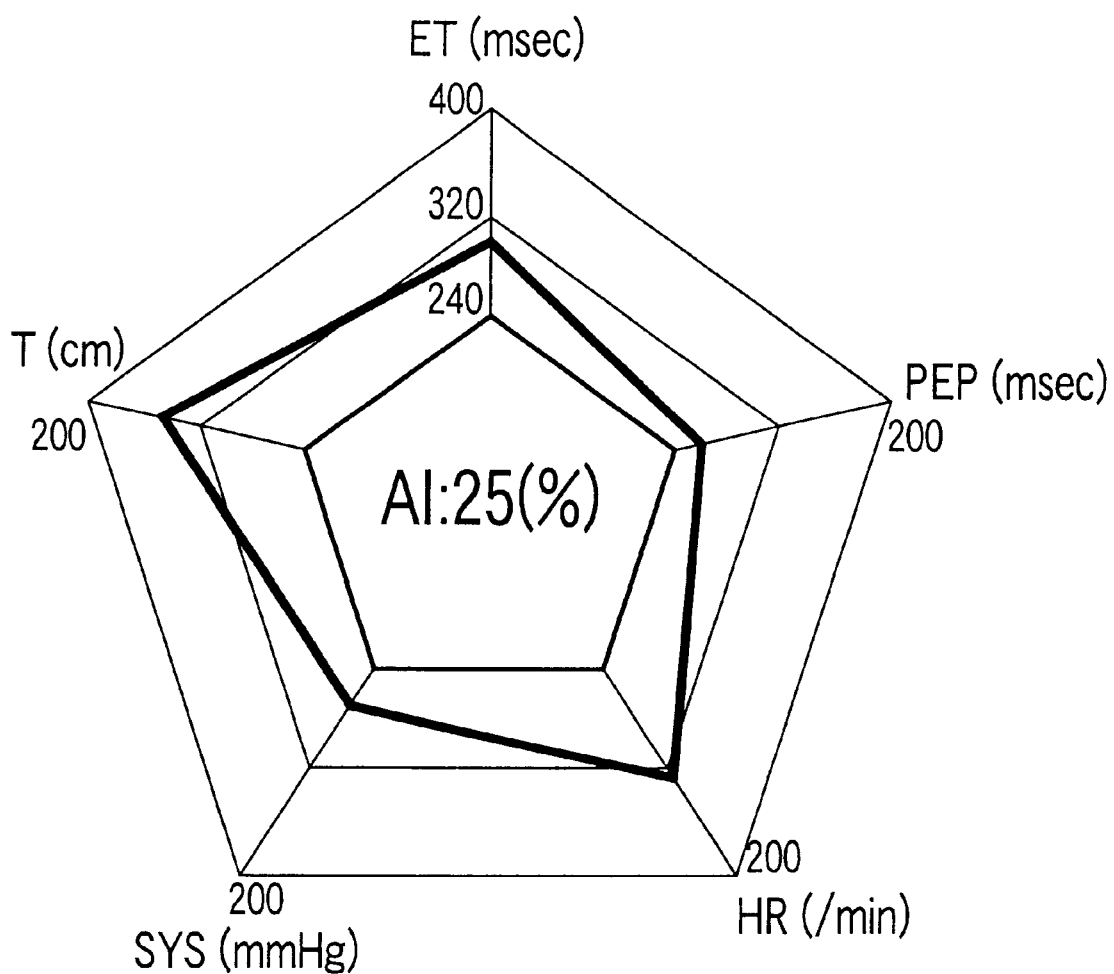
FIG. 10 is a radar chart displayed at Steps S23 and S24 of FIG. 9.

Next, the control goes to S23 corresponding to the augmentation-index displaying means 98. At S23, the CPU operates the display device 79 to display the augmentation index AI determined at S13, at a prescribed position on a screen of the display 79. Subsequently, the control goes to S24 corresponding to the waveform-related-information displaying means 100. At S24, the CPU operates the display device 79 to display respective graphical representations of the stature T determined at S2, the heart rate HR determined at S14, the ejection time ET determined at S15, and the systolic blood pressure $BP_{SYS}$ determined at S20. FIG. 10 shows a radar chart (i.e., a pentagonal graph) that is displayed by the displayed device 79 at S23 and S24. The augmentation index AI is displayed at the center of the radar chart.

In the embodiment employing the above-described flow charts, the control device 32 determines, at S2, S14, S15, S16, and S20 (the waveform-related-information obtaining means), the stature T, the heart rate HR, the ejection time ET, the pre-ejection period PEP, and the systolic blood pressure $BP_{SYS}$ each of which is related to change of the shape or waveform of the carotid pulse wave wc. In addition, the control device operates, at S24 (the waveform-related-information displaying means 100), the display device 79 to display, in addition to the augmentation index AI, the stature T, the heart rate HR, the ejection time ET, the pre-ejection period PEP, and the systolic blood pressure $BP_{SYS}$. Thus, when a medical person inspects arteriosclerosis of the subject based on the augmentation index AI, the person can additionally take into account the stature T, the heart rate HR, the ejection time ET, the pre-ejection period PEP, and the systolic blood pressure $BP_{SYS}$ of the subject. Thus, the person can make a more accurate diagnosis on the arteriosclerosis based on the augmentation index AI.

Additionally, in the embodiment employing the above-described flow charts, the control device 32 operates, at S24 (the waveform-related-information displaying means 100), the display device 79 to display, in addition to the augmentation index AI, the stature T, the heart rate HR, the ejection time ET, the pre-ejection period PEP, and the systolic blood pressure $BP_{SYS}$ in the single radar chart. Thus, the medical person can easily recognize, at a glance, all of the stature T, the heart rate HR, the ejection time ET, the pre-ejection period PEP, and the systolic blood pressure $BP_{SYS}$.

Hereinafter, there will be described another embodiment of the present invention. The same reference numerals as used in the above-described, first embodiment are used to designate the corresponding elements of the present, second embodiment, and the description thereof is omitted.

Figure 11:
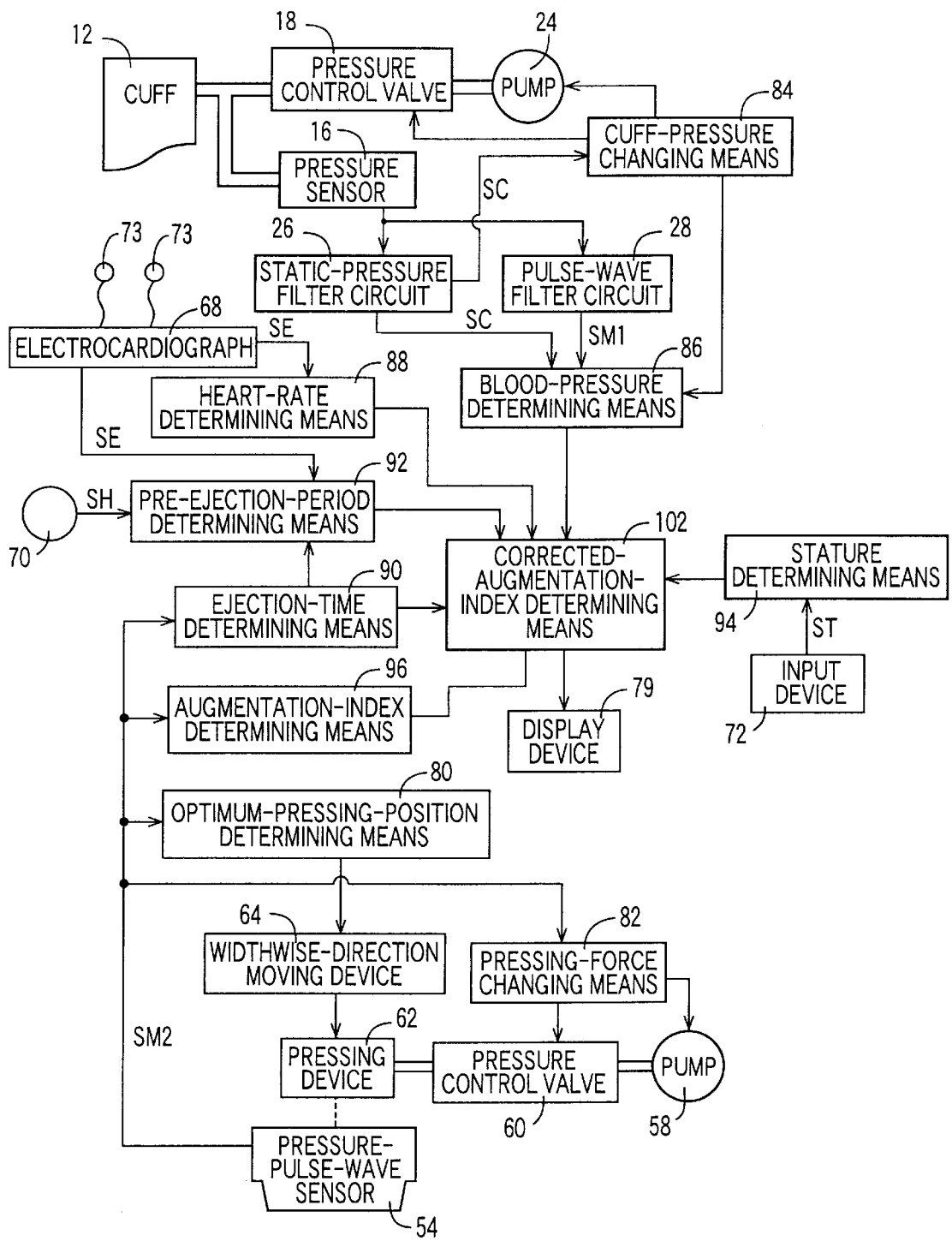
FIG. 11 is a block diagram for explaining essential control functions of an electronic control device of a different arteriosclerosis inspecting apparatus than the apparatus of FIG. 1.

The second embodiment relates to a different arteriosclerosis inspecting apparatus than the apparatus 10 shown in FIG. 1, and FIG. 11 is a block diagram for explaining essential control functions of an electronic control device 32 of the present, second apparatus. The second apparatus differs from the first apparatus 10 only with respect to the control functions of the control device 32 of the second apparatus. The control functions of the control device 32 of the second apparatus differs from those of the control device 32 of the first apparatus, in that the former control functions employ a corrected-augmentation-index determining means 102 in place of the augmentation-index displaying means 98 and the waveform-related-information displaying means 100 of the latter control functions. Accordingly, the corrected-augmentation-index determining means 102 will be described below.

The corrected-augmentation-index determining means 102 corrects the augmentation index AI determined by the augmentation-index determining means 96, into a corrected augmentation index AI' that would be determined by the means 96 if the systolic blood pressure $BP_{SYS}$ determined by the blood-pressure determining means 86, the heart rate HR determined by the heart-rate determining means 88, the ejection time ET determined by the ejection-time determining means 90, the pre-ejection period PEP determined by the pre-ejection-period determining means 92, and the stature T determined by the stature determining means 94 are would be equal to respective pre-set standard values. The blood-pressure determining means 86, the heart-rate determining means 88, the ejection-time determining means 90, the pre-ejection-period determining means 92, and the stature determining means 94 are each a sort of waveform-related-information obtaining means. A manner in which the corrected-augmentation-index determining means 102 determines the corrected augmentation index AI' will be described in detail by reference to the flow chart shown in FIG. 12.

Figure 12:
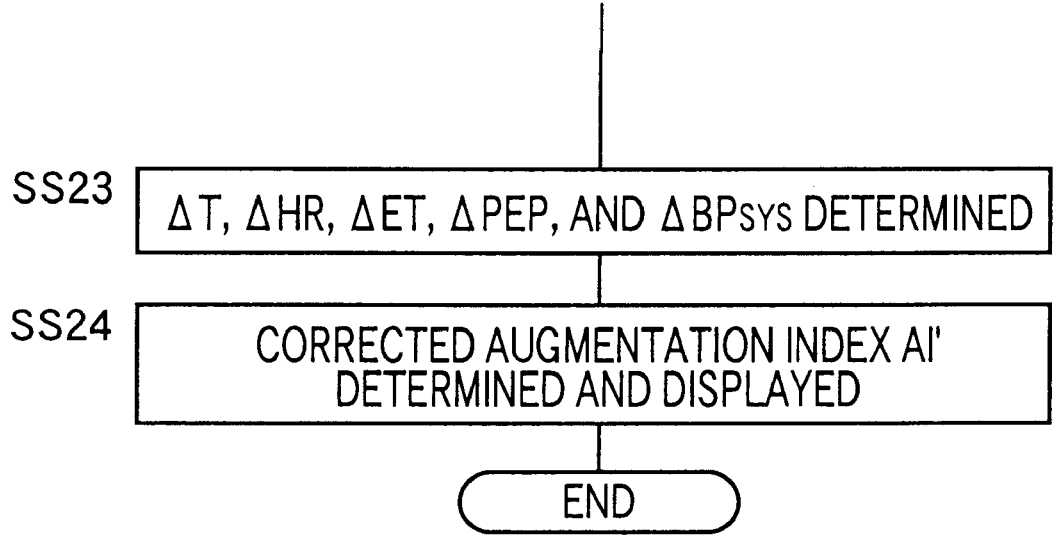
FIG. 12 is a flow chart for explaining more concretely the control functions of a CPU of the control device, shown in FIG. 11.

The flow chart of FIG. 12 includes 22 steps, not shown, that are identical with S1 to S22 shown in FIGS. 8 and 9, and employs SS23 and SS24 in place of S23 and S24 shown in FIG. 9. At SS23, the control device 32 or the CPU 76 determines a difference between each of the stature T determined at S2, the heart rate HR determined at S14, the ejection time ET determined at S15, the pre-ejection period PEP determined at S16, and the systolic blood pressure $BP_{SYS}$ determined at S20 and a corresponding one of respective standard values that are experimentally determined, in advance. More specifically described, the CPU determines a stature difference $\Delta T$ by subtracting, from the stature T determined at S2, the standard value determined in advance for stature T, and likewise determines a heart-rate difference $\Delta HR$, an ejection-time difference $\Delta ET$, a pre-ejection-period difference $\Delta PEP$, and a systolic-blood-pressure difference $\Delta BPL_{SYS}$. Then, at SS24, the CPU substitutes the augmentation index AI determined at S13, and the stature difference $\Delta T$, the heart-rate difference $\Delta HR$, the ejection-time difference $\Delta ET$, the pre-ejection-period difference $\Delta PEP$, and the systolic-blood-pressure difference $\Delta BPL_{SYS}$, determined at SS23, for the following Expression 2 representing a corrected-augmentation-index determining formula, so as to determine a corrected augmentation index AI':

$$AI' = AI + a\Delta T + b\Delta HR + c\Delta ET + d\Delta PEP + e\Delta BPL_{SYS} \quad \text{(Expression 2)}$$

where a, b, c, d, and e are constants that are experimentally determined in advance.

The corrected-augmentation-index determining formula represented by Expression 2 corrects the augmentation index AI into the corrected augmentation index AI', such that the greater the difference between the actually obtained waveform-related information, such as the actually determined stature T, and the standard value pre-determined for the waveform-related information is, the greater the difference between the augmentation index AI and the corrected augmentation index AI' is. Thus, the corrected augmentation index AI' determined according to Expression 2 is equal to an augmentation index AI that would be determined when the waveform-related information would be equal to the standard value.

In the embodiment employing the above-described flow chart of FIG. 12, the control device 32 corrects, at SS23 and SS24 (the corrected-augmentation-index determining means 102), the augmentation index AI into the corrected augmentation index AI' that would be determined if the waveform-related information would be equal to the pre-set standard value. Therefore, based on the corrected augmentation index AI', arteriosclerosis can be inspected with improved accuracy.

While the present invention has been described in its preferred embodiment by reference to the drawings, it is to be understood that the invention may otherwise be embodied.

For example, in the illustrated arteriosclerosis inspecting apparatus 10, the pressure-pulse-wave detecting probe 36 for detecting the carotid pulse wave wc is employed as the pulse-wave detecting device. However, the pulse-wave detecting device may be one which detects a pulse wave from a different portion than the neck portion 38; such as an upper arm, a wrist, a femoral portion, or an ankle of the subject.

In addition, in the illustrated arteriosclerosis inspecting apparatus 10, the five sorts of waveform-related information, i.e., the stature T, the heart rate HR, the ejection time ET, the pre-ejection period PEP, and the systolic blood pressure $BP_{SYS}$ are determined. However, the number of the sorts of waveform-related information is not limited to that number. For example, it is possible to obtain only a single sort of waveform-related information.

Generally, the denominator of the augmentation-index calculating formula (Expression 1) used to determine the augmentation index AI is the pulse pressure PP. However, the pulse pressure PP of Expression 1 may be replaced with the amplitude (i.e., the magnitude) of the carotid pulse wave wc at the time of occurrence of the peak point of the incident-wave component thereof, because the formula employing the amplitude as the denominator indicates arteriosclerosis.

The corrected-augmentation-index calculating formula represented by Expression 2 may be replaced with that represented by the following Expression 3 for use in calculating a corrected augmentation index AI':

$$AI' = (1 + a_1\Delta T + b_1\Delta HR + c_1\Delta ET + d_1\Delta PEP + e_1\Delta BPL_{SYS}) \times AI \quad \text{(Expression 3)}$$

where $a_1$, $b_1$, $c_1$, $d_1$, and $e_1$ are constants that are experimentally determined in advance.

The present invention may be embodied with other various changes without departing from the spirit of the invention.

What is claimed is:

1. An apparatus for inspecting arteriosclerosis of a living subject, comprising:

a pulse-wave detecting device which detects a pulse wave from a portion of the subject;

an augmentation-index determining means for determining, based on the pulse wave detected by the pulse-wave detecting device, an augmentation index indicating a proportion of a reflected-wave component of the pulse wave to an incident-wave component thereof, so that the arteriosclerosis of the subject is inspected based on the augmentation index determined by the augmentation-index determining means;

at least one waveform-related-information obtaining device which obtains at least one sort of waveform-related information that is related to a change of a waveform of the pulse wave detected by the pulse-wave detecting device;

a display device;

an augmentation-index displaying means for operating the display device to display the augmentation index determined by the augmentation-index determining means; and a waveform-related-information displaying means for operating the display device to display, in addition to the augmentation index, the waveform-related information obtained by the waveform-related-information obtaining device.

2. An apparatus according to claim 1, comprising a plurality of waveform-related-information obtaining devices which obtain a plurality of sorts of waveform-related information, respectively, each of which is related to the change of the waveform of the pulse wave detected by the pulse-wave detecting device, wherein the waveform-related-information displaying means operates the display device to display, in addition to the augmentation index, the plurality of sorts of waveform-related information obtained by the plurality of waveform-related-information obtaining devices.

3. An apparatus according to claim 1, wherein the waveform-related-information obtaining device obtains, as the waveform-related information, at least one of a systolic blood pressure, a heart rate, an ejection time, a pre-ejection period, and a stature of the subject.

4. An apparatus according to claim 2, wherein the waveform-related-information displaying means operates the display device to display, in addition to the augmentation index, a multidimensional graphical representation of the plurality of sorts of waveform-related information obtained by the plurality of waveform-related-information obtaining devices.

5. An apparatus according to claim 2, wherein the plurality of waveform-related-information obtaining devices obtain, as the plurality of sorts of waveform-related information, at least two parameters of a systolic blood pressure, a heart rate, an ejection time, a pre-ejection period, and a stature of the subject.

6. An apparatus according to claim 4, wherein the plurality of waveform-related-information obtaining devices obtain, as the plurality of sorts of waveform-related information, at least three parameters of a systolic blood pressure, a heart rate, an ejection time, a pre-ejection period, and a stature of the subject, and wherein the waveform-related-information displaying means operates the display device to display, in addition to the augmentation index, a radar chart having at least three axes indicative of said at least three parameters, respectively.

7. An apparatus for inspecting arteriosclerosis of a living subject, comprising:

a pulse-wave detecting device which detects a pulse wave from a portion of the subject;

an augmentation-index determining means for determining, based on the pulse wave detected by the pulse-wave detecting device, an augmentation index indicating a proportion of a reflected-wave component of the pulse wave to an incident-wave component thereof;

at least one waveform-related-information obtaining device which obtains at least one sort of waveform-related information that is related to a change of a waveform of the pulse wave detected by the pulse-wave detecting device; and a corrected-augmentation-index determining means for correcting, based on the waveform-related information obtained by the waveform-related-information obtaining device, the augmentation index into a corrected augmentation index which is determined by the augmentation-index determining means when the waveform-related information obtained by the waveform-related-information obtaining device is equal to a pre-set standard value, so that the arteriosclerosis of the subject is inspected based on the corrected augmentation index determined by the corrected-augmentation-index determining means.

8. An apparatus according to claim 7, further comprising a display device which displays the corrected augmentation index determined by the corrected-augmentation-index determining means, so that the arteriosclerosis of the subject is inspected based on the corrected augmentation index displayed by the display device.

* * * * *